United States Patent [19]
Saunders

[11] Patent Number: 5,536,246
[45] Date of Patent: Jul. 16, 1996

[54] BACK SUPPORT SYSTEM WITH INTERCHANGEABLE AND POSITIONALLY ADJUSTABLE ORTHOTIC SUPPORTS

[75] Inventor: Harold D. Saunders, Eden Prairie, Minn.

[73] Assignee: The Saunders Group, Inc., Chaska, Minn.

[21] Appl. No.: 393,531

[22] Filed: Feb. 23, 1995

Related U.S. Application Data

[60] Division of Ser. No. 852,295, Mar. 16, 1992, Pat. No. 5,399,150, which is a continuation-in-part of Ser. No. 719,267, Jun. 21, 1991, Pat. No. 5,205,815.

[51] Int. Cl.⁶ ..................................... A61F 5/00
[52] U.S. Cl. ............................ 602/19; 2/44; 128/101.1
[58] Field of Search ....................... 602/19; 128/100.1, 128/101.1, 96.1, 898; 450/94, 95, 110, 112, 121, 149, 154; 2/44

[56] References Cited

U.S. PATENT DOCUMENTS

| | | |
|---|---|---|
| 1,599,688 | 9/1926 | Sullivan . |
| 2,088,302 | 7/1937 | McKeever . |
| 2,232,246 | 2/1941 | Klein . |
| 2,249,198 | 7/1941 | Carter . |
| 2,481,396 | 9/1949 | Cohen . |
| 2,553,353 | 5/1951 | Binder et al. . |
| 2,641,258 | 6/1953 | Rutledge . |
| 2,910,984 | 11/1959 | Yeakey et al. . |
| 3,029,814 | 4/1962 | Kravitz . |
| 3,141,457 | 7/1964 | Davidson . |
| 3,234,937 | 2/1966 | Nelkin . |
| 3,434,469 | 3/1969 | Swift . |
| 3,441,027 | 4/1969 | Lehman . |
| 3,454,003 | 7/1969 | Sailhen . |
| 3,526,229 | 9/1970 | Blair . |
| 3,554,190 | 1/1971 | Kaplan . |
| 3,756,247 | 9/1973 | Hand . |
| 3,920,008 | 11/1975 | Lehman . |
| 4,175,553 | 11/1979 | Rosenberg . |
| 4,400,832 | 8/1983 | Kinder . |
| 4,475,543 | 10/1984 | Brooks et al. . |
| 4,572,167 | 2/1986 | Brunswick . |
| 4,833,730 | 5/1989 | Nelson . |
| 4,836,194 | 6/1989 | Sebastian et al. . |

(List continued on next page.)

FOREIGN PATENT DOCUMENTS

| | | |
|---|---|---|
| 0410904 | 1/1991 | European Pat. Off. . |
| 1290920 | 3/1962 | France . |
| 2243787 | 11/1991 | United Kingdom . |

OTHER PUBLICATIONS

Managing Lower Back Pain, 2d Ed., W. H. Kirkaldy–Willis, Churchill Livingstone, 297–303 (1988).
Camp Therapy Product Price List, Camp International, Inc. (Jun. 1988).
News Release Re: Dyna–Life™ Active Support Belt, Physical Therapy Products, 59 (Mar. 1991).
Saunders Therapy Products 1991 Catalog, pp. 26, 27, 28, 35.

*Primary Examiner*—Linda C. Dvorak
*Attorney, Agent, or Firm*—Mueting, Raasch, Gebhardt & Schwappach

[57] ABSTRACT

A lumbosacral back support system with interchangeable and positionally adjustable lumbosacral orthopedic support members for supporting the spine of a user during physical activity, specifically for athletes and industrial workers. A back support band is provided with a first releasable attachment mechanism. A lumbosacral support member with second releasable attachment mechanism is provided for engagement with the first releasable attachment mechanism. The first and second releasable attachment mechanisms are arranged for attaching a lumbosacral support member to the back support band at a variety of positions relative to the spine of the user. The releasable attachment mechanism of the present invention provides the user the option to substitute different lumbosacral support members on the back support band. Additionally, the back support band may be releasably attach to a compression-type short to further secure the lumbosacral back support system to the user.

7 Claims, 5 Drawing Sheets

U.S. PATENT DOCUMENTS

| | | |
|---|---|---|
| 4,907,576 | 3/1990 | Curlee . |
| 4,926,845 | 5/1990 | Harris . |
| 4,941,237 | 7/1990 | Hovis . |
| 5,040,524 | 8/1991 | Votel et al. . |
| 5,086,759 | 2/1992 | Buddingh . |
| 5,147,261 | 9/1992 | Smith et al. . |
| 5,148,549 | 9/1992 | Sydor . |
| 5,188,585 | 2/1993 | Peters . |

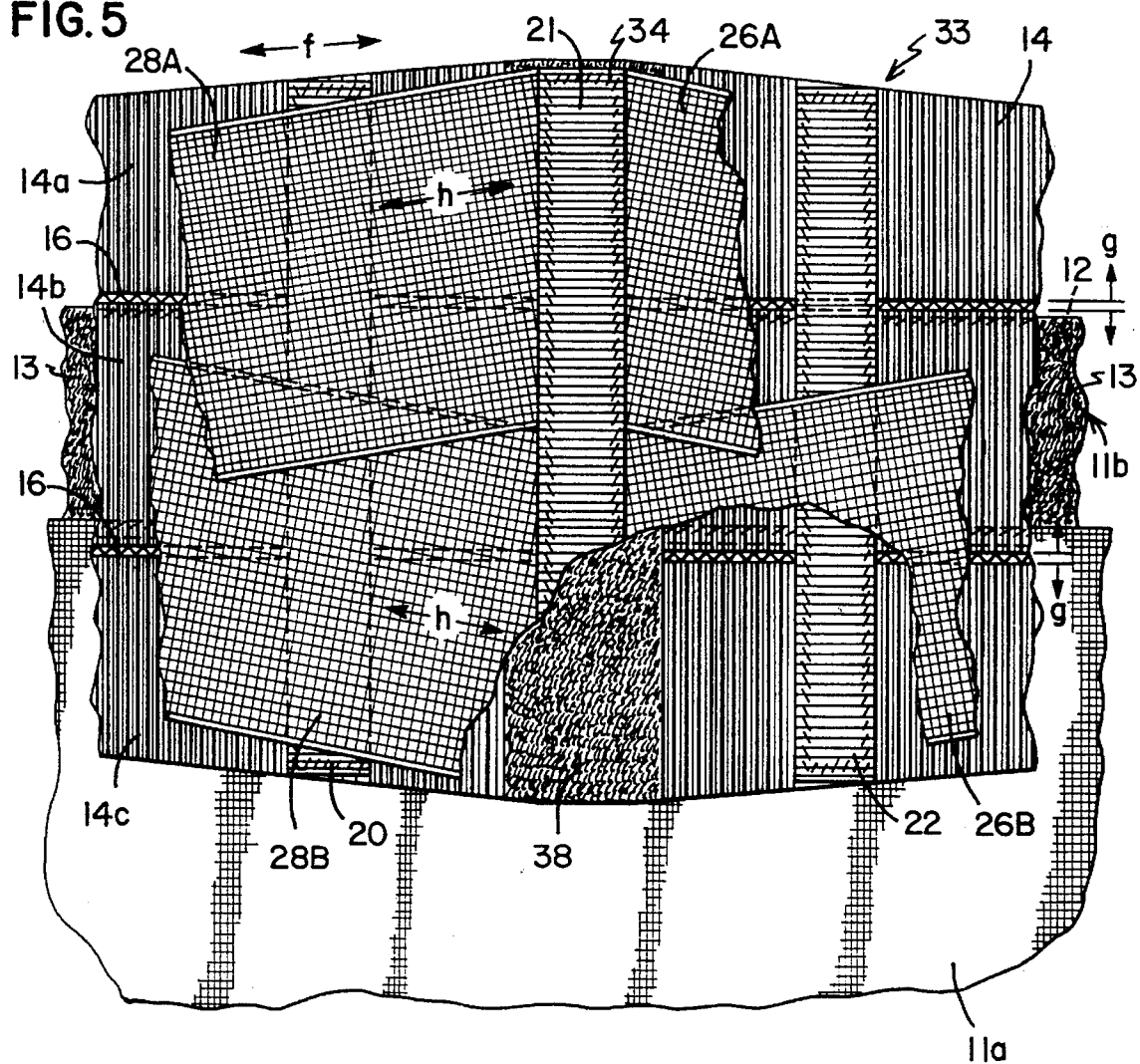
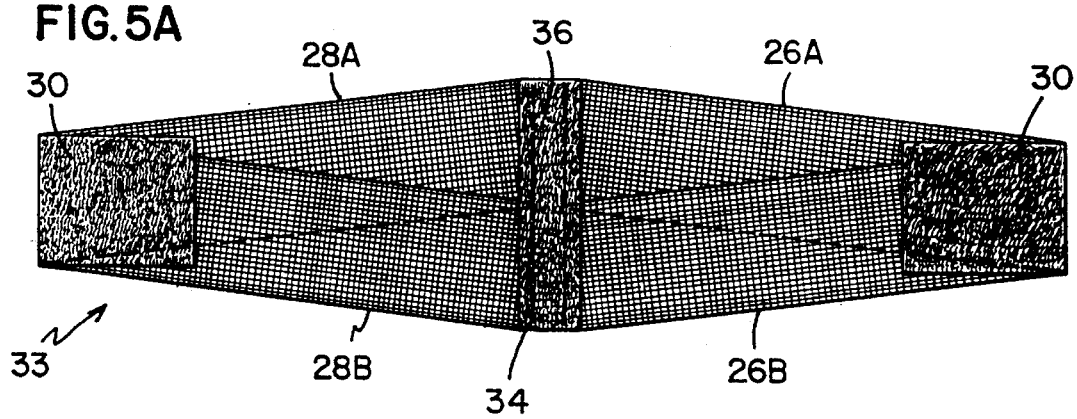

5,536,246

BACK SUPPORT SYSTEM WITH INTERCHANGEABLE AND POSITIONALLY ADJUSTABLE ORTHOTIC SUPPORTS

This is a division of application Ser. No. 07/852,295, filed Mar. 16, 1992, now U.S. Pat. No. 5,399,150, which is a continuation-in-part of Ser. No. 07/719,267, now U.S. Pat. No. 5,205,815.

BACKGROUND OF THE INVENTION

1. Field of the Invention

This invention relates generally to a lumbosacral back support for medical or industrial applications, and more specifically, to a back support with interchangeable and positionally adjustable lumbosacral orthopedic support members.

2. Description of the Art

Lower back disorders and the pain associated therewith have become epidemic in today's society. Such disorders are typically caused by a combination of poor posture, faulty body mechanics, stressful living and working habits, loss of flexibility and a general decline in physical fitness. In general, the best non-surgical management techniques for such disorders include proper strengthening exercises, treatment and rest, and back-care education. However, there are many instances in which orthopedic devices or orthoses in the form of lumbosacral braces can be effectively used to supplement such management techniques or to help prevent injury or reinjury to the lower back. Orthotic devices are particularly useful in reducing mobility of the spine joints so as to reduce the amount of intervertebral bending and intervertebral torsion in the regions where the back support is applied. Orthotic devices also function to lessen the average axial loading and bending loading on the spine, thereby, avoiding or reducing strain and aggravation to the spine during physical activity. Such orthoses (typically referred to as "back-brace") devices are also helpful in reminding the wearer of the fact that an injury has taken place and that he should not make sudden motions that will override the protective mechanisms of his body. Orthopedic devices also provide protection against rapid dynamic motions that occur during strenuous athletic or industrial activity.

Prior orthotic devices also lack the versatility to accommodate a wide range of patient needs. Prior art devices tend to be rigidly structured to provide a particular level of support at a fixed location. However, each patient will have different needs with regard to the level and location of support required from the orthotic device. The required level of support may also vary with the particular activity performed.

Further, some patients may want the option to affix, remove or adjust the orthotic device on short notice. However, since most orthotic devices are worn under clothing, the user must disrobe to make adjustments. For example, athletes and industrial workers may only need to wear the orthotic device for brief periods or need to adjust the level of support quickly.

The need for a particular level and/or location of support may change over time for an individual patient. Therefore, the ideal orthopedic treatment may require a variety of orthotic devices for a particular patient. However, having to substitute different orthotic devices over the course of treatment is extremely costly and inconvenient to the patient.

Another aspect of the above problem is that the need for such orthotic devices is particularly acute for those involved in strenuous athletic or industrial work activities which place abnormal stress and strain on the spine. In performing their required functions, such individuals do not always have the opportunity to observe desired back safety and protection guidelines and often need the additional support and protection provided by an orthopedic orthosis.

A number of styles of lower back support orthoses have been known in the art. Such devices, which are typically configured to provide sacroiliac support or support for the lumbar spine region, have generally been effective for use by those who are not involved in any physical activity involving rapid movement. However, for those activities involving strenuous motion including stretching, twisting or jumping, which may for example be experienced by basketball players, hockey players or golfers, such standard orthotic devices have a tendency to migrate or ride up on the body of the wearer. To be effective in providing relief or support to the lower spine, such devices necessarily partially encircle the pelvis and hips and at least partially overlie the upper buttocks region of the wearer, which naturally tends to urge the orthosis upward on the body during physical activity. On an active wearer, it does not take long for such orthosis to rapidly migrate upward on the body, thereby decreasing its effectiveness and becoming very uncomfortable for the wearer. In such instances, the orthosis becomes more of an impediment to the wearer than an aid.

Efforts have been made in the art to maintain the desired position of the orthosis on the body. Crotch, groin and leg straps secured to the lower edges of the orthotic device have been used in an attempt to keep the device from riding up on the wearer's body. Shoulder straps are often used to prevent the orthotic device from moving downward on the patient during times of inactivity.

Such retaining structures, however, have been largely unacceptable to active wearers such as athletes and industrial workers, due to discomfort and irritation. These retaining structures make it extremely inconvenient and time consuming for the user to affix, remove or adjust the orthotic device to their body. Because of the inconvenient retaining structures of prior art devices, active users are often left with the option of wearing the orthotic device for extended periods, even when it is not required, or not wearing it when it is required.

Finally, in addition to the requirements for lower back support, active athletes also have a need for support of their upper thighs (i.e., hamstring and quadriceps muscles), their abdomen muscles and their groin area muscles. While earlier techniques typically required individual support structures for each such set of muscles, modern "compression" shorts or liners constructed of nylon/Spandex® or cotton/poly/Lycra® fabrics have been found to be effective in simultaneously providing graduated compression and support to the hamstring, quadriceps, groin area and abdominal muscles, while yielding superior flexibility and comfort over prior art individual support techniques. Heretofore, however, no attempt has been made to combine an interchangeable and positionally adjustable orthotic support with the benefits offered by compression shorts.

The present invention provides a back support band with interchangeable and positionally adjustable orthotic lumbar support straps. Alternatively, the back support band may be releasably attached to a compression-type short which holds the support band in place during strenuous activity and simultaneously provides support to the upper thigh, groin area and abdominal muscles.

SUMMARY OF THE INVENTION

The present invention relates to a lumbosacral back support with interchangeable and positionally adjustable lumbosacral orthopedic support members.

The present invention is intended to support the spine of a user during physical activity, specifically for medical and industrial applications. A back support band extends circumferentially around the body of the user and is preferably configured to support the lumbosacral spine region of the user's body. The back support band is provided with a first releasable attachment mechanism. The lumbosacral support straps with a second releasable attachment mechanism are provided for engagement with the first releasable attachment mechanism. The first and second releasable attachment mechanisms are arranged for attaching lumbosacral support straps to the back support band at a variety of positions relative to the spine of the user.

The first and second releasable attachment mechanisms provide the user the option to substitute different lumbosacral support straps on the back support band.

Alternatively, the back support band may be releasably attached to a compression-type short so that the back support band is securely positioned on the user.

The back support band may alternatively be circumferentially discontinuous and have a fastener for adjusting the degree of compression the back support band provides to the user. An adjustable back support band is particularly well suited for supporting the user's spine even when the adjustable strap member is detached. The support band may further comprise a plurality of interconnected circumferential bands arranged to support the lumbosacral spine region of the user. Additionally, the lumbosacral support system of the present invention may optionally include a plurality of flexible stay members or other rigid members to enhance the support capabilities.

One method for using the present invention involves attaching lumbosacral support straps to the back support band at a first position using the first and second releasable attachment mechanism, and then, when required, detaching the lumbosacral support straps from the first position and reattaching the lumbosacral support straps to the back support strap at a second position by engaging the first and second releasable attachment mechanisms.

An alternate method of using the present invention involves attaching a first set of lumbosacral support straps to the back support band using the first and second releasable attachment mechanisms and then, when required, detaching the first lumbosacral support straps and attaching a second set of lumbosacral support straps to the back support band by engaging the first and second releasable attachment mechanisms.

BRIEF DESCRIPTION OF THE DRAWINGS

Referring to the drawings, wherein like numerals represent like parts throughout the several views:

FIG. 5 is an enlarged fragmentary view, with sections thereof broken away of the back portion of a preferred lumbosacral back support system of FIG. 4;

FIG. 5A illustrates the inside surface of the preferred support strap assembly which may be attached to the back support band of FIG. 5;

DETAILED DESCRIPTION OF THE PREFERRED EMBODIMENT

Figures 1, 2:
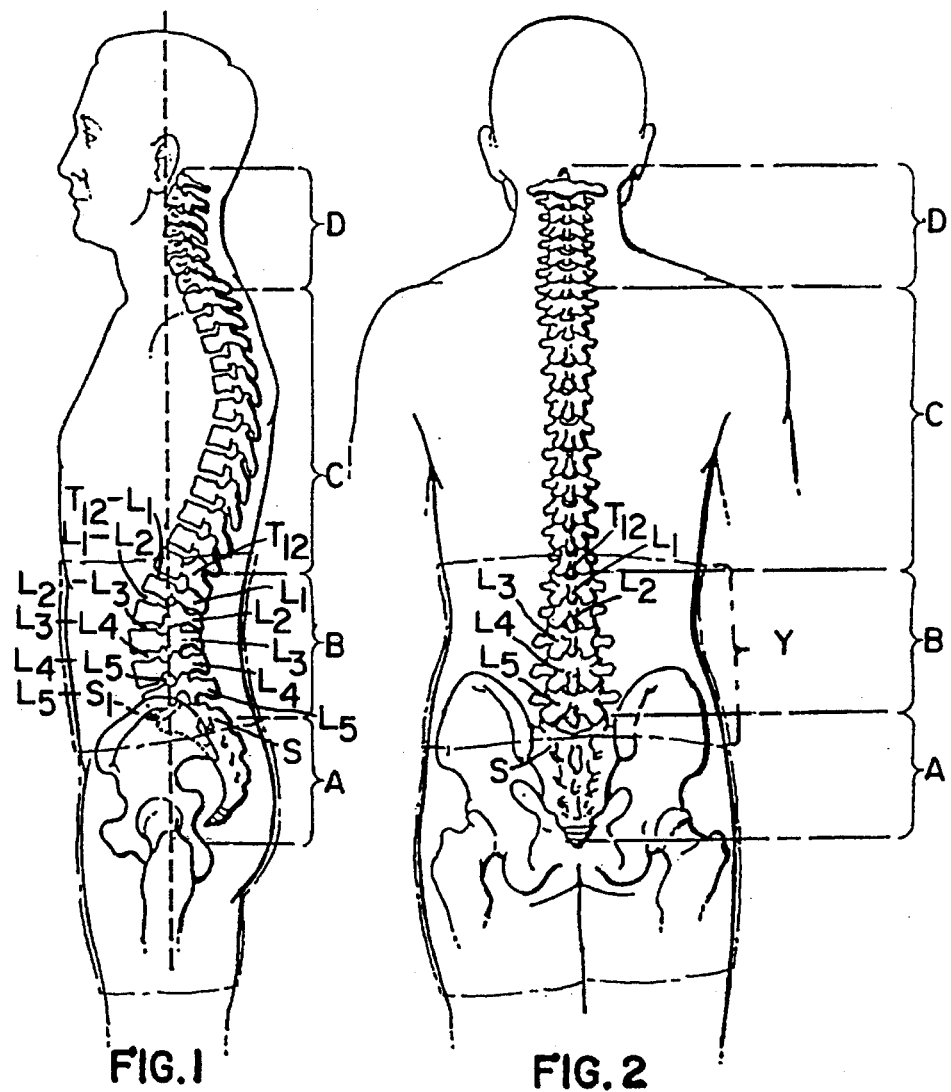
FIG. 1 is a diagrammatic side view representation of a human body illustrating the four defined physiological curve regions of the spine.
FIG. 2 is a diagrammatic representation of the human body of FIG. 1, illustrated from a back or posterior view.

Diagrammatic views of a human body, generally illustrating the spinal column and its orientation and position relative to the sacrum and ilium of the sacroiliac region of the body are illustrated in FIGS. 1 and 2. FIGS. 1 and 2 will be used to facilitate describing placement of the lumbosacral back support system of this invention relative to the human body and to the vertebrae of the spinal column. It is not the intent of this specification to describe the operation or medical disorders associated with the spinal column, it being understood that those skilled in the art are knowledgeable in such matters and/or need not be knowledgeable in the physiological peculiarities of the human body in order to effectively use the present invention. For a more detailed description, however, of the physiological anatomy of the spinal column and of the various musculoskeletal disorders associated therewith, the reader is referred to the text *Evaluation, Treatment and Prevention of Musculoskeletal Disorders* by H. Duane Saunders, Educational Opportunities, 1985. To the extent that any of the materials of my above-identified book are relevant to an understanding of the art, or of the use or applicability of my invention to providing support for the spinal vertebrae of the human body, they are herein incorporated by reference.

In general, with reference to FIGS. 1 and 2, the spine has four curved areas generally designated at "A, B, C and D". The sacral curved region "A" comprising the fused bones of the sacrum is convex posteriorly. The lumbar region of the spine, generally designated at "B" is concave posteriorly. The thoracic region of the spine "C" is convex posteriorly. The cervical region of the spine, generally designated at "D" is concave posteriorly. This invention focuses primarily in providing support for those portions "A" and "B" of the spinal column referred to as the lumbosacral region. The lumbar region generally includes five vertebrae generally labeled "$L_1$" through "$L_5$" in FIGS. 1 and 2. The $L_5$ lowermost vertebra of the lumbar region lies adjacent the sacrum "S" and is separated thereby by spinal joint labeled "$L_5$-$S_1$". The uppermost vertebra "$L_1$" of the lumbar region lies adjacent to and is separated from the lowermost vertebra "$T_{12}$" of the thoracic region by the joint labeled as "$T_{12}$-$L_1$". While there is some dispute as to the relative percentages of lumbar flexion/extension of the various joints in the lumbar region, most authorities agree that most of the flexion/extension takes place at the "$L_4$-$L_5$" and the "$L_5$-$S_1$" joints.

It will be understood by those skilled in the art that the lumbosacral back support system of the present invention may also be referred to as a lumbar support orthosis. As will be discussed in detail below, the lumbosacral support system of the present invention may consist of a number of components. In the preferred embodiment, these components are generally an adjustable support strap assembly releasably attached to an adjustable support band having a plurality of flexible stay members. The back support band may optionally be releasably attached to a compression-type short to securely position the lumbosacral back support system on the user.

In the first embodiment, the lumbosacral back support system preferably contains an adjustable support strap assembly having a first end, middle portion and second end. A second releasable attachment mechanism is located proximate the middle portion of the adjustable support strap assembly. The first releasable attachment mechanism is located proximate the back portion of the back support band. A fastening device is provided at the first end and second end of the adjustable support straps for adjusting the degree of compression around the user's back.

In the second embodiment, the back support band may be releasably attached to a compression-type short to securely position the back support band on the user.

In the third preferred embodiment, the lumbosacral support system may comprise an adjustable back support band with a vertical split along the front portion. The edges of the vertical split are provided with an appropriate detachable fastener material so that the user can adjust the pressure. The adjustable support strap assembly is attached to the adjustable support band as discussed above.

In the fourth embodiment, the adjustable back support band is releasably attached to a compression-type short in a manner similar to that of the second preferred embodiment. The user also has the option to use the adjustable back support band with or without the adjustable support straps.

The compression-type short preferably comprises elastic material which is elastic in the directions of two mutually orthogonal axes of the material. The compression-type short may include leg portions which are designed and configured to extend at least partially down the thigh region of the wearer, to support the thigh and groin area muscles. The compression-type short may be configured as a brief, and may or may not include an access fly.

The lumbosacral back support system preferably includes one or more stay members, which distribute pressure throughout the lumbosacral spine region of the user. The lumbosacral back support system may also include a removable insert member to provide additional support.

The preferred embodiments are constructed to enable the lumbosacral back support system to be accurately aligned with the user's body to maximize the desired degree of immobilization of the lumbar vertebrae. Further, the adjustable support straps may be easily removed and replaced with other support straps, or easily repositioned to a location more suited to the user's needs. Finally, the entire lumbosacral back support system is constructed of appropriate materials and is designed so as to maximize comfort to the wearer, even during vigorous physical activity, while achieving its functional purposes.

Figure 3:
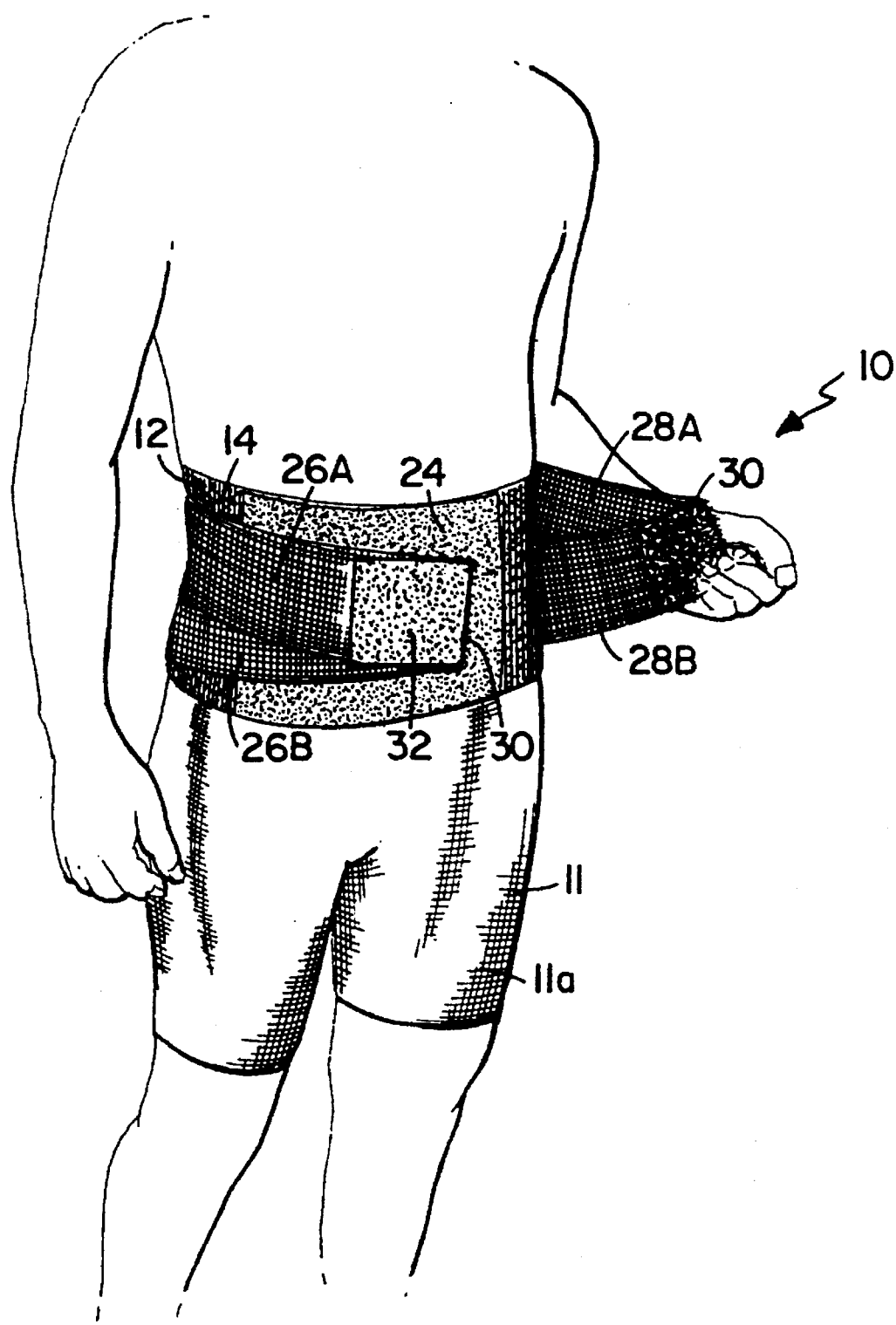
FIG. 3 is a front perspective view of a first and second embodiment of a lumbosacral back support system of the present invention illustrated as it would be operatively positioned on a human body.

For purposes of the discussion below, the lumbosacral back support system 10 of the first and second embodiment will be similar, except that the second embodiment includes releasable attachment to a compression-type short 11. Referring to FIG. 3, the first and second embodiments of a lumbosacral back support system configured according to the principles of the present invention are generally illustrated at 10. In the first embodiment, the lumbosacral back support system 10 generally comprises a back support band 14 with a series of adjustable support straps 26A, 26B and 28A, 28B. The operation of the first embodiment will be discussed in detail below. It will be understood from the discussion below that the compression shorts 11 are not part of the first embodiment.

In the second embodiment, also illustrated in FIG. 3, the back support band 14 may be attached to the compression-type short 11 with a releasable attachment mechanism, such as Velcro®, discussed in detail below. Preferably, the releasable attachment mechanism would be configured to allow adjustment of the back support band 14 with respect to the compression short 11. Further, the releasable attachment mechanism allows different back support bands 14 to be substituted, depending on the needs of the user. In an alternate preferred embodiment, the back support band 14 may be permanently attached to the compression-type short 11.

Figures 4, 7, 9:
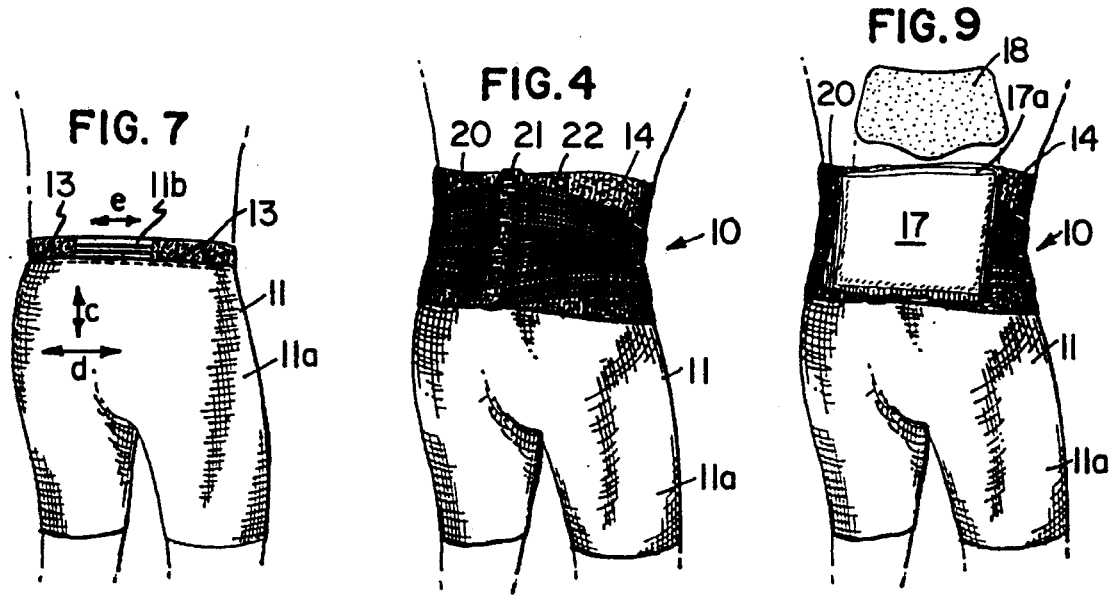
FIG. 4 is a back perspective view of the preferred lumbosacral back support system of FIG. 3.
FIG. 7 is a back view illustrating a preferred compression short for use with the lumbosacral back support system of FIG. 4.
FIG. 9 is a back perspective view with portions thereof broken away of the lumbosacral back support system of FIG. 4 modified to include an insertable thermoform moldable insert.
Figure 6:
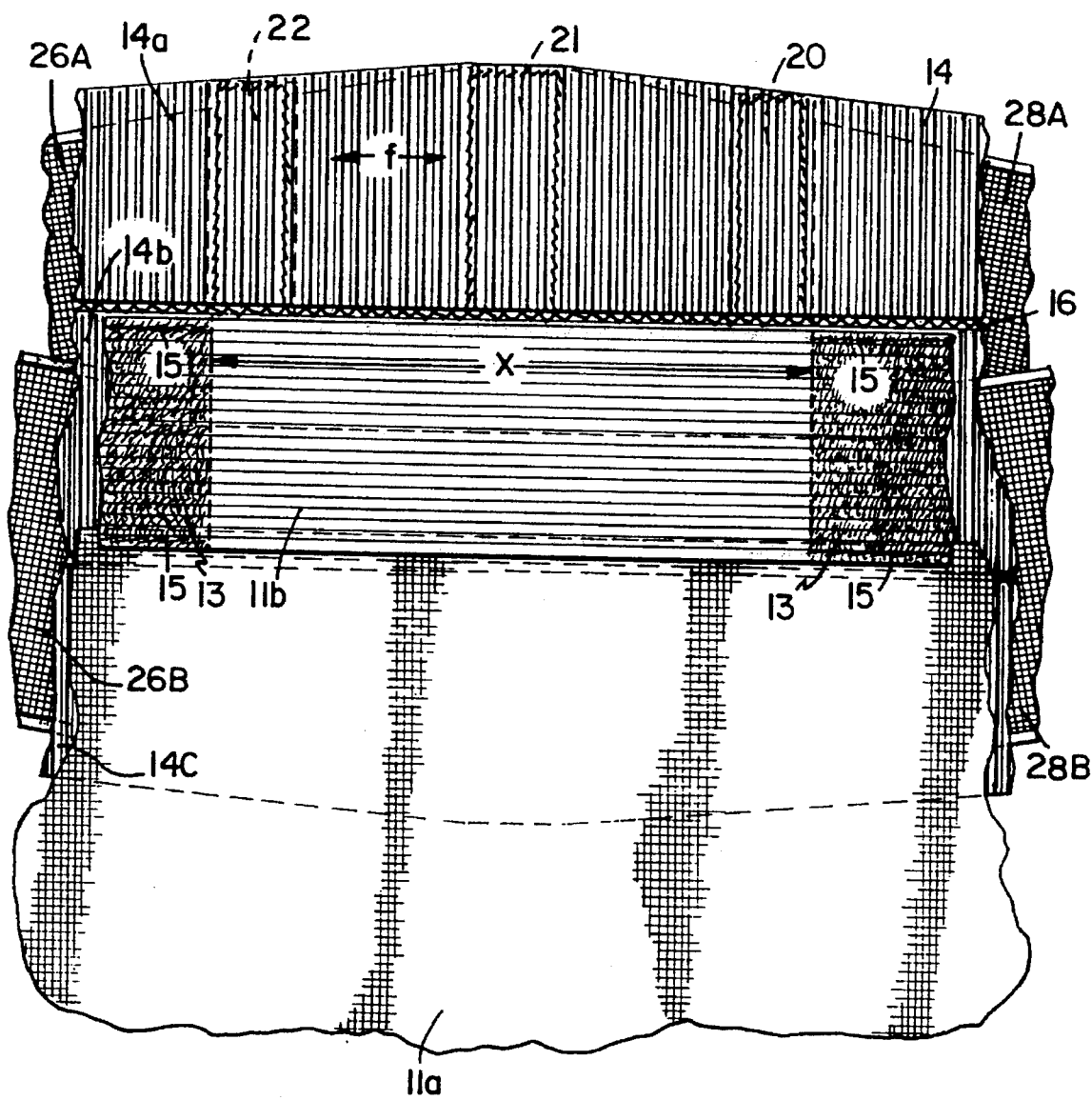
FIG. 6 is an enlarged fragmentary view of a preferred lumbosacral back support system of FIG. 5, illustrated from the opposite interior side thereof.

The waistband 11b of the compression-type short 11 preferably includes the hook portion 13 of a hook-and-loop fastener, such as Velcro® as illustrated in FIG. 7. The hook portion 13 preferably does not extend along the back portion of the compression-type short 11. In the preferred embodiments, that portion of the hook portion 13 not extending around the waist band 11b is illustrated in FIG. 6 at "x".

The back support band 14 is preferably sized to encircle the body of the wearer and has a circumference slightly larger than that of the waistband 11b of the compression short portion 11. The inner surface of the back support band 14 would include the loop-portion 12 (see FIG. 5) of the hook-and-loop fastener for attachment of the back support band 14 to the compression-type short.

The preferred compression short 11 of the second preferred embodiment is separately illustrated in FIG. 7 as it would appear positioned on a human body. The compression short 11 preferably comprises a short or pant-shaped lower portion 11a of light to medium weight elastic material appropriately stitched to form the short configuration and having elasticity in both the warp and weft directions of the material, generally running in the directions of the arrows "c" and "d" of FIG. 7. The elastic material 11a may be of any appropriate type which provides the desired compressive support to the body, yet is comfortable to wear. Examples of materials which are known to be suitable for the purpose include cotton/poly/Lycra® fabric and nylon/Spandex® material. Both offer the desired four-way stretch and provide graduated compression and support to the hamstring, quadriceps, groin area and abdominal muscles encircled thereby. The pant-shaped portion 11a is secured near its upper end by a circumferential waistband 11b of elastic material. The elastic waistband 11b is primarily only elastic in the direction indicated by the arrow "e" in FIG. 7. The length of the leg portions of the compression pant portion 11a preferably extends from the crotch area to a mid-thigh position so as to give compressive support to both the hamstring and the quadriceps muscles of the wearer.

It will be understood from a more complete description of the preferred embodiments, however, that the above principles would apply equally well to a compression pant configuration having truncated leg portions which terminate adjacent the crotch area, typically referred to as a "jockey-brief" configuration. Such configuration, while providing less support to the hamstring and quadriceps muscles still provides support for the groin area muscles and accomplishes the purposes of maintaining the upper lumbosacral back support system 10 in operative position during strenuous activity of the wearer.

The first and second preferred embodiments of the lumbosacral back support system 10 are illustrated in FIGS. 3–6. For purposes of the discussion below, the operation of the lumbosacral back support system 10 of the first and second embodiment will be similar, except that the second embodiment includes releasable attachment to a compression-type short 11.

As best illustrated in FIG. 5, the elastic circumferential back support band 14 preferably comprises three individual support bands 14a, 14b and 14c, circumferentially joined by cross-stitching 16 along their respective adjacent edges, to collectively comprise the back support band 14. The individual support bands 14a, 14b and 14c may be of the same or different circumferential lengths. The material of the bands 14a, 14b and 14c is of relatively heavyweight elastic material with elasticity preferably running only in the directions of the arrow "f".

The cross-stitching 16 between the multiple bands 14a, 14b and 14c provides limited inter-band elasticity in the direction indicated by the arrows "g" to enable the multiple-band configuration to more readily conform to the body contours of the wearer. It will be understood by those skilled in the art that the particular construction of the back support band 14 is not to be limited to that herein described for the preferred embodiment. For example, while a multiple-band configuration has been illustrated, a single-band configuration could also be employed. Similarly, while a multiple-band configuration comprising three interconnected bands has been illustrated, any number of such bands or strips of material comprising a multiple-band configuration could be employed to better conform to the body of the user.

In the preferred embodiments, the inner surfaces of the bands 14a, 14b and 14c are lined with a soft elastic surface to provide additional comfort to the wearer and to prevent irritation and chafing of the wearer's body as the back support band 14 moves against the body in operative use. The soft elastic material of a type sold under the HELANCA® trademark is known to be suitable for this purpose. The soft elastic surface is particularly important when the back support band 14 is worn directly on the body, without the compression-type short 11.

A plurality of flexible stay members 20, 21 and 22 are preferably securely attached in generally vertical alignment in circumferentially spaced positions along the posterior portion of the back support band 14. While FIG. 5 illustrates the flexible stay members 20, 21, and 22 all of the same length, it will be recognized that different length stays may be preferable for particular users. Alternatively, the flexible stay members 20, 21, and 22 may be attached to the adjustable support straps 26 and 28, discussed in detail below.

In the preferred embodiments illustrated, the central stay member 21 may be operatively positioned for direct vertical alignment with the spinal column of the wearer, and the stay members 20 and 22 are configured so as to be vertically aligned slightly to either side of the spinal column. The length of the stay members generally corresponds to the width or height of the back support band 14. It will be understood by those skilled in the art, however, that there need not be an identical correspondence in such dimensions and that the number and relative spacing of such stay members may vary. The length of the stay members 20–22 and their relative operative position with respect to the vertebrae of the spinal column of the wearer may be the same as previously discussed with respect to the width or height dimensions of the back support band 14 and its positioning relative to the spinal column of the user. The stay members may be of any appropriate semi-rigid material such as plastic or metal.

The stays are preferably made from hardened, galvanized spring steel round wire which is coiled and flattened, and is generally referred to in the trade as "spiral boning". Such material provides support rigidity for partially immobilizing the spinal column vertebrae, yet can be flexed, when placed under pressure, to conform to the body contours of the wearer, as illustrated in FIG. 4.

Referring to FIG. 6, relating to the second preferred embodiment, the "x" dimension portion of the waistband 11b where the hook portion 13 is not present corresponds generally to the spacing between the outermost stay members 20 and 22. This configuration enables the stay members to be pulled into snug engagement with the wearer's body adjacent the spinal column, without imparting corresponding circumferential tension to the waistband portion 11b of the compression short 11 of a nature that would tend to cause binding or gathering of the waistband.

As illustrated in FIGS. 5 and 5A, the adjustable support straps 26 and 28 are joined at a seam 34 to form a single support strap assembly 33. The individual support straps 26A, 26B and 28A, 28B are constructed of relatively stiff elastic material which is elastic primarily only in the direction as indicated by the arrows "h" in FIG. 5. The individual support straps 26A, 26B and 28A, 28B are tapered as they proceed from the seam 34 toward a pair of Velcro panels 30, as illustrated in FIG. 5A.

FIG. 5A shows the inside surface of the support strap assembly 33, which is designed to be releasably attached to the back support band 14. Preferably, the hooked portion 36 of a hook-and-loop fastener mechanism is attached to the inside surface of the support strap assembly 33 along the seam 34. Alternatively, separate adjustable support straps having suitably located Velcro® may be overlapped with one another to form substantially the support strap assembly 33 illustrated in FIG. 5A. The corresponding looped portion 38 is attached to the back support band 14, in alignment with the centrally positioned stay member 21, as illustrated in FIG. 5. Although a variety of attachment mechanisms are possible, the preferred hooked portion 36 and loop portion 38 are sold under the tradename Velcro®.

It will be appreciated that the hook 36 and loop 38 portions of the releasable Velcro® attachment mechanism do not have to be in complete alignment to provide adequate attachment force between the support strap assembly 33 and the back support band 14. Further, the relative size of the hook 36 and loop 38 portions provides additional flexibility in locating the support strap assembly 33 relative to the back support band 14.

Referring now to FIG. 3, a panel of fastener material 24 is secured to the front portion of the back support band 14. In the preferred embodiment, the fastener material 24 comprises a sheet of "looped" material suitable for engagement by a corresponding hooked fastener, discussed above. The adjustable support straps 26 and 28 taper from the posterior of the lumbosacral back support system toward their free ends and overlap one another (as illustrated in FIG. 3), each terminating at the Velcro® hook fastener member 30. In FIG. 3, the tapered end of the support strap 26 is illustrated as secured by its Velcro® hook fastener 30 to the looped fastener panel 24. The support strap 26 also includes a smaller panel of looped fastener material 32 secured to its outer surface. The Velcro® hook fastener material of the support strap 28 can be secured either to the larger panel 24 of looped fastener material, to the smaller panel 32 of looped fastener material, or to both, as is clearly illustrated in FIG. 3.

In the embodiments illustrated in FIGS. 3 and 5, the support straps 26 and 28 are spaced relative to one another so as to extend the full width or height of the back support band 14. However, the height or width of the back support band 14 can vary, depending upon the size of the user or the orthopedic requirements. For an adult, the support band width or height is preferably between 8 and 12 inches.

More important, however, than the height or width dimensions of the back support band 14 is the location of the back support band 14 in relation to the spine of the wearer. With reference to FIGS. 1 and 2, the support band height (illustrated in phantom at 14) should preferably be designed to extend on the wearer such that its lower edge extends to the sacrum and even more preferably to the middle of the sacrum, and such that its upper edge at least covers the first two joints ($L_4$-$L_5$ and $L_3$-$L_4$) of the lumbar region. More preferably still, the upper edge should extend so as to cover all five vertebrae and all of the intervening joints of the lumbar region, as illustrated by the dimension "y" in FIG. 2.

The releasable attachment mechanism 36, 38 on the support strap assembly 33 allows the user to locate the support strap assembly 33 at the ideal location for his or her orthopedic needs. In particular, the releasable attachment mechanism operates adequately even if the hook 36 and loop 38 portions are only partially overlapped. For example, the support strap assembly 33 may be located at a variety of positions relative to the vertical axis of the user's spine. Further, the ease with which the support strap assembly 33 is removed allows the user to quickly substitute an alternate support strap assembly 33 without removing the back support band 14 or compression short 11. The ability to interchange the support strap assemblies 33 or adjust the location of the support strap assembly 33 relative to the user's spine allows the lumbosacral back support system of the present invention to satisfy the changing needs of an individual user.

To operate the first embodiment of the present invention, the user places the lumbosacral back support system 10 in operative position by removing the support strap assembly 33 from the back support strap 14 and pulling the back support band 14 over his legs up to his waist area. In such position, the back support band 14 and its secured stay members 20, 21 and 22 are properly aligned with the wearer's spinal column so as to support the lumbosacral vertebrae and joints of the wearer as hereinbefore described.

The support strap assembly 33 is then positioned at the desired location, causing engagement of the hook portion 36 on the support strap 33 with the loop portion 38 on the back support band 14. The desired pressure is generated by first pulling and securing the support strap 26 in the position as illustrated in FIG. 3, and by subsequently pulling and securing the support strap 28 and its hook fastener 30 into overlapping engagement with the loop fastener member portion 32 and the primary loop fastener panel portion 24. The pressure from the support straps 26 and 28 bring the stays 20, 21 and 22 into firm engagement with the user's back.

When thus secured, the stay members 20, 21, and 22, in combination with the adjustable support straps 26 and 28 and the underlying circumferential back support band 14, serve to partially immobilize the motion of the lumbosacral vertebrae, thereby reducing the amount of interspine bending and interspine torsion in such regions and decreasing the pressures acting on the intervertebral disks. The combined forces of the elastic circumferential back support band 14 and the adjustable support straps 26, 28 also provide abdominal support.

Due to the strength of the releasable attachment mechanism 36 and 38, the adjustable support straps 26, 28 are securely fixed at the desired support position on the user. The soft lining material of the circumferential back support band 14 maximizes comfort to the wearer throughout his active movements. The interchangeable and positionally adjustable nature of the adjustable support straps 26 and 28 enable the degree of immobilization support provided to the spinal column and the amount of support provided to the abdomen to be varied according to the needs of the user.

In the second embodiment, the user would first pull the compression-type short 11 over his legs up to his waist area. It is contemplated that the compression short portion 11 would be manufactured in a number of different sizes such that waistband 11b of the compression short member is aligned generally with the waist of the wearer. Next, the back support band 14 is pulled over the legs and positioned relative to the user's spine. Releasably attaching the back support band 14 will provide maximum flexibility in adjusting its location and allowing different back support bands 14 to be substituted, depending on the needs of the user. Finally, the adjustable support straps 26 and 28 are attached to the back support band 14 as discussed above. It will be understood that the elastic nature of the compression short 11 provides graduated compression support for the groin area, abdominal, hamstring and quadriceps muscles.

Figure 8:
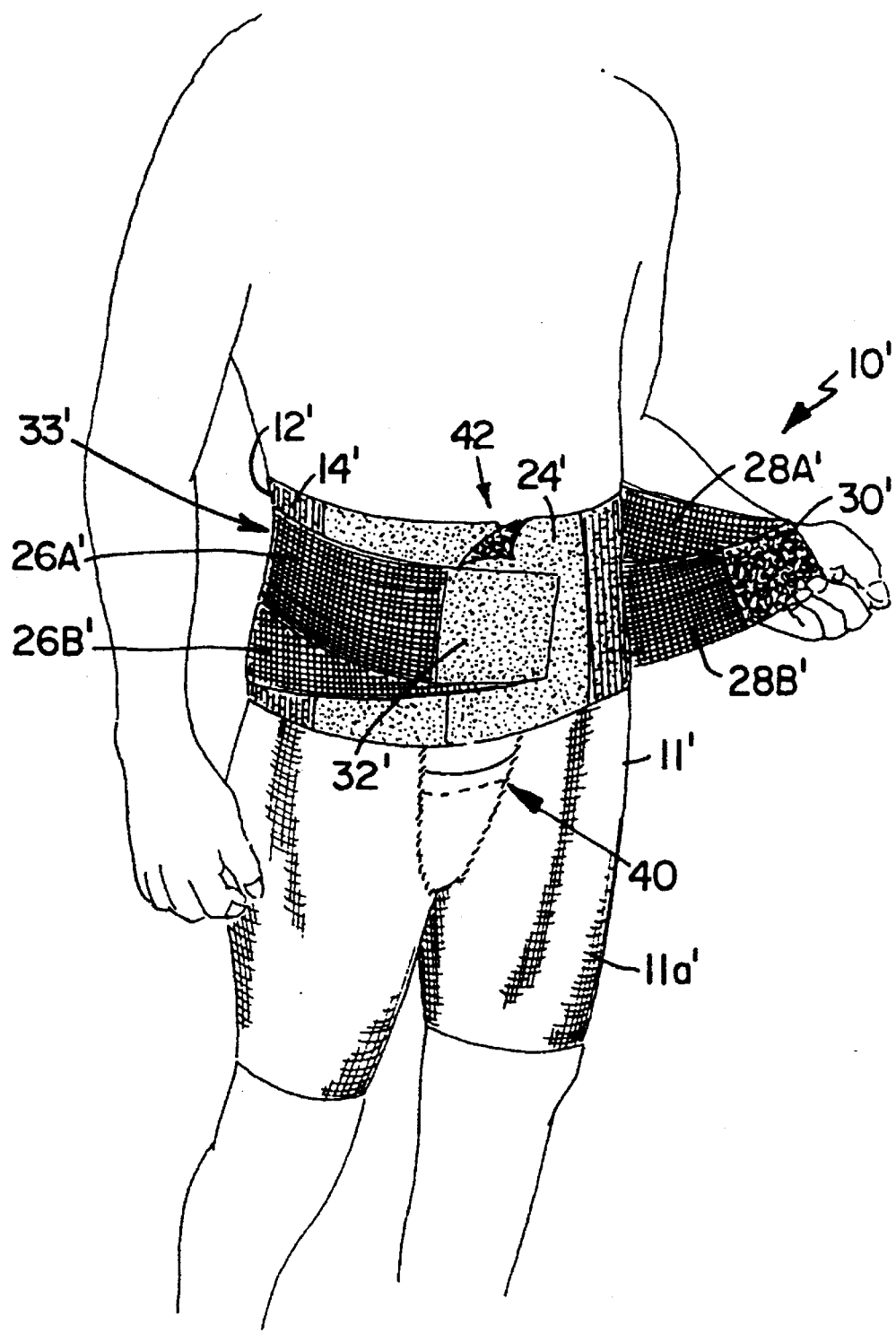
FIG. 8 is a front perspective view of a third and fourth embodiment of a preferred lumbosacral back support system with an adjustable back support band.

Third and fourth embodiments of a lumbosacral back support system 10' are illustrated in FIG. 8. The same numerical terminology for similar lumbosacral back support system portions has been maintained between the first and second embodiments of the lumbosacral back support systems, with the addition of a "prime" designation for the second embodiment numbers. All features discussed with respect to the first and second embodiments are assumed to be present in the third and fourth embodiments, unless otherwise specified. As with the first and second embodiment, the third embodiment encompasses a lumbosacral back support system 10' without a compression-type short 11', while the fourth embodiment includes the short 11'.

The major advantage of the lumbosacral back support system 10' of the third and fourth embodiments is that the back support band 14' is provided with a vertical split 42 along the front portion thereof for adjusting the pressure provided by the back support band 14'. Consequently, it will be appreciated that the lumbosacral back support system 10' illustrated in FIG. 8 may be used with or without the adjustable strap members 26' and 28'.

The ends of the elastic back support band 14' proximate the vertical split 42 are preferably detachably secured to one another by appropriate fastener material, such as the Velcro® hook and looped material discussed above. The adjustable back support band 14' enables the user to adjust the pressure on the flexible stays and the degree of compression around the user's waist, independent of the support strap assembly 33'. The adjustable back support band 14' provides additional adjustment capabilities for the lumbosacral back support system 10' in addition to that provided by the support strap assembly 33'.

In an alternative fourth embodiment, the adjustable back support band 14' may serve the combined function as the back support band 14 and adjustable support strap straps 26 and 28 of the first three embodiments. This feature is particularly important since users will often find that their need for support varies substantially with the activity being performed. Some users may be able to rely on the lumbosacral support provided by the back support band 14' without use of the support straps 26' and 28'.

A number of additional features may be added, and changes made to either of the above-described embodiments. An example of one such additional feature is diagrammatically illustrated in FIG. 9. Referring thereto, the lumbosacral back support system 10 may be modified to include a pocket or pouch 17 attached to the "inside" surface of the back support band 14. Such pouch may be integrally formed within the back support band 14 or adjustable support straps 26 and 28. The pocket 17 may be oriented so as to address the lumbosacral region of the wearer's spine and is positioned between the back support band 14 and the waist-band 11b.

The pocket 17 has an upper access port 17a that may accommodate appropriate closure means and is sized and configured to cooperatively accept a thermoform moldable insert member 18. Insert 18 is illustrated in FIG. 9, removed from the pocket 17. Such insert members generally have an inner core of thermoplastic material having a peripheral shape that conforms to the general contour of the lower back, and an outer coating of foam padding or other material to enhance wearer comfort. Upon application of heat, the thermoplastic of the insert becomes pliable and can be molded to the desired orthotic shape that uniquely "fits" the lumbosacral back region of the wearer. Upon cooling, the insert retains its molded shape. While such inserts can assume any desired size and shape, in the preferred embodiment the insert has a "width" that spans virtually the entire back area of the wearer and a "height" that is approximately the same as that of the back support band 14.

The second and fourth embodiments of a lumbosacral back support system 10 or 10' may also include a fly configuration generally designated at 40 in the compression-type short portion 11', as illustrated in FIG. 8. The preferred fly portion 40 generally comprising a horizontal access port through the elastic material 11a' of the compression short portion 11' and disposed at a position such that the groin support properties of the compression short are retained. While a horizontal fly configuration has been illustrated, it will be understood by those skilled in the art that other fly configurations could equally well be used.

It will be appreciated that the preferred lumbosacral back support systems provide the combined benefits of a back support band with interchangeable and positionally adjustable lumbosacral support straps. The releasable attachment mechanism used to attach the support strap assembly 33 to the back support band 14 provides sufficient stability of the lumbosacral back support system 10 so that the user can engage in active movement. The preferred embodiments provide for versatile alignment, adjustment or substitution of the primary lumbar support portions of the lumbosacral back support system. Additionally, the lumbosacral back support system 10 may include a compression-type short to secure the back support band 14 to users who engage in strenuous activity.

While the present invention will be described with respect to its use for medical and industrial applications, it will be understood that the invention is not to be so limited, but can be used by any individual requiring or desiring the combined support features offered by this invention. Further, the embodiments which include a compression-type short are particularly suited to users engaged in athletic activity.

While the preferred embodiments are described with respect to particular brands and types of materials, it will be understood by those skilled in the art that the invention is not to be limited by any particular type or brand of material, but that such materials are used for descriptive purposes only. Further, while the invention will be described with regard to a particular style of compression short and with regard to such a compression short having a particular leg configuration, that the invention is not to be so limited, but applies equally well to shorts/pants of various styles and configurations and to those having, for example, longer or shorter leg segments. Further, while the invention will be described with respect to a particular style of lumbar support orthosis using a particular number and style and configuration of vertical stay members, it will be understood by those skilled in the art that the invention is not limited, other than as claimed, to the particulars of the orthosis structures described in the preferred embodiments. Further, while the present invention will be described with respect to a lumbosacral back support system which has a primary function of providing support for the lumbar spine region, it will be understood that additional support structures such as those specifically developed for sacroiliac support could be incorporated within the overall structure of the lumbosacral back support system. These and other modifications and applications of the invention will become apparent to those skilled in the art in light of the following description of preferred embodiments of this invention.

Other modifications of the invention will be apparent to those skilled in the art in view of the foregoing descriptions. These descriptions are intended to provide specific examples of embodiments which clearly disclose the present invention. Accordingly, the invention is not limited to the described embodiments or to the use of specific elements, dimensions, materials or configurations contained therein. All alternative modifications and variations of the present invention which fall within the spirit and broad scope of the appended claims are covered.

What is claimed is:

1. A method for adjusting an orthopedic back support comprising the steps of:

providing a compression short with a front and back portion, said compression short having a first releasable attachment means;

providing a lumbosacral support having a second releasable attachment means for engaging with said first releasable attachment means, said first and second releasable attachment means arranged for attaching said lumbosacral support to said compression short at a variety of positions;

attaching said lumbosacral support to said compression short at a first location by engaging said first and second releasable attachment means;

detaching said lumbosacral support from said first location on said compression short; and attaching said lumbosacral support to said compression short at a second location by engaging said first and second releasable attachment means.

2. A method for adjusting an orthopedic back support comprising the steps of:

providing a compression short with a front and back portion, said compression short having a fist releasable attachment means;

providing a first lumbosacral support having a second releasable attachment means for engaging with said first releasable attachment means, said first and second releasable attachment means arranged for attaching said lumbosacral support to said compression short at a variety of positions;

attaching said lumbosacral support to said compression short by engaging said first and second releasable attachment means;

detaching said first lumbosacral support from said compression short;

providing a second lumbosacral support having third releasable attachment means for engaging with said first releasable attachment means, said first and third releasable attachment means arranged for attaching said lumbosacral support to said compression short at a variety of positions; and attaching said second lumbosacral support to said compression short by engaging said first and third releasable attachment means.

3. A method for attaching an adjustable lumbosacral back support system to a user, the user having an upper body, a lower body, and a waist portion, the user also having pants with a waist portion and an upper body garment with a lower portion, comprising the steps of:

providing a compression short having elastic means for conforming said compression short tightly to the pelvis, groin area and lower abdominal muscles of the user, a front, a back, and a top portion, the compression short further having a first releasable attachment means proximate the top portion;

providing a lumbosacral support band for extending circumferentially around the waist portion of the user, the support band having a middle circumferential region, an inner and outer surface, and a second releasable attachment means attached to the inner surface proximate the middle circumferential region for engaging with the first releasable attachment mean;

engaging the compression short with the user so that the first releasable attachment means extends above the waist portion of the user and the lower portion of the upper body garment is retained between the top portion of the compression short and the waist portion of the user;

engaging the pants with the lower body of the user over the compression short so that the top portion of the compression short extends above the waist portion of the pants; and engaging the first and second releasable attachment means so that the adjustable support band may be adjusted without removing the pants or upper body garment.

4. The method of claim 3 further including the steps of:

providing a third releasable attachment means on the outer surface of the support band proximate the back portion of the compression short;

providing at least one adjustable strap member having a first end, a middle portion, a second end, and a fourth releasable attachment means located proximate the middle portion, the strap member further including fastening means attached to the first and second ends thereof for adjustably closing the adjustable strap member around the user's waist; and attaching the adjustable strap member to the support band by engaging the third and fourth releasable attachment means, whereby the adjustable support strap member may be adjusted without removing the pants or upper body garment.

5. A method for attaching an adjustable lumbosacral back support system to a user, comprising the steps of:

providing a compression short having attaching means proximate a top edge, a body portion and elastic means for conforming said compression short tightly to the pelvis, groin area and lower abdominal muscles of the user, and a lumbosacral support band for extending circumferentially around the waist portion of the user, the support band having an upper, a lower, a middle circumferential portion, and an outer surface;

operatively connecting the middle circumferential portion of the support band to the attaching means on the compression short so that the lower circumferential portion of the support band is not connected to the body portion of the compression short; and engaging the compression short with the user.

6. The method of claim 5 further including the steps of:

providing a first releasable attachment means on the outer surface of the support band proximate the back portion of the compression short;

providing at least one adjustable strap member having a first end, a middle portion, a second end, and a second releasable attachment means located proximate the middle portion, the strap member further including fastening means attached to the first and second ends thereof for adjustably closing the adjustable strap member around the user's waist; and attaching the adjustable strap member to the support band by engaging the first and second releasable attachment means, whereby the adjustable support strap member may be adjusted or moved vertically on the user without removing the pants or upper body garment.

7. A method for applying a lumbosacral back support system for support the spine of a user during physical activity comprising:

applying a compression short to a user, the compression short having a waist band and elastic means for conforming the compression short tightly to the pelvis, groin area and lower abdominal muscles of the user the compression short having attachment means for receiving a lumbosacral support member at a plurality of positions; and attaching a lumbosacral support member to the attachment means of the compression short extending from proximate the sacrum to at least the L3 lumbar vertebra whereby the compression short maintains the vertical position of the lumbosacral support member relative to the user's spine during physical activity.

* * * * *